United States Patent [19]

Angeles

[11] 4,446,076
[45] May 1, 1984

[54] METHOD OF PREPARING 1,2-DIBROMO-2-CYANO-(SUBSTITUTED)-ALKANE ANTIMICROBIAL COMPOUNDS

[75] Inventor: Marshall R. Angeles, Scotchplains, N.J.

[73] Assignee: Merck & Co., Inc., Rahway, N.J.

[21] Appl. No.: 333,274

[22] Filed: Dec. 22, 1981

[51] Int. Cl.³ .............. C07C 120/00; C07C 121/16; C07C 121/46; C07C 121/66
[52] U.S. Cl. .............................. 260/465 G; 544/402; 546/330; 548/214; 548/215; 548/240; 548/300; 548/372; 548/566; 549/74; 549/491; 260/464; 260/465 F; 260/465.7
[58] Field of Search ............... 260/464, 465.7, 465 G; 548/566, 240, 214, 215, 372, 300; 549/491

[56] References Cited

U.S. PATENT DOCUMENTS 3,608,084  9/1971  Matt .................................. 424/304
3,644,380  2/1972  Harmetz et al. ............. 260/465.7 X
3,849,422  11/1974  Weis ............................. 260/465.7 X

OTHER PUBLICATIONS

Migrdichian, "The Chemistry of Organic Cyanogen Compounds", (1947), A.C.S. Monograph Series, No. 105, p. 259.
Lespieau et al., Organic Synthesis, p. 209, Collective vol. I, 2nd Edition, (Feb. 1967), Gilman & Blatt, Ed.
Lespieau et al., Organic Synthesis, Collective vol. I, 2nd Edition, (Feb. 1967), Gilman & Blatt, Ed., p. 186.
Grignard, Compt. Rend. 152:388–390 (1911).
Grignard, et al., Ann. de chim. 4:28–57 (1915).

Primary Examiner—Joseph Paul Brust
Attorney, Agent, or Firm—Michael C. Sudol, Jr.; R. Brent Olson; Raymond M. Speer

[57] ABSTRACT

Method of preparing antimicrobial compounds of the formula:

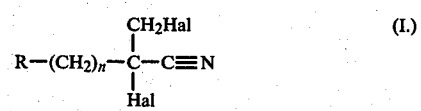

comprising the following steps:
(1) halogenating allyl halide to form 1,2,3-trihalopropane; (2) dehydrohalogenating the 1,2,3-trihalopropane to form 2,3-dihalo-1-propene;
(3) treating the 2,3-dihalo-1-propene with a Grignard reagent of the formula R—MgHal, where R is as defined above, followed by treatment with magnesium, to form 3-(R-substituted)-2-magnesiumhalide)-1-propene;
(4) treating the 3-(R-substituted)-2-(magnesiumhalide)-1-propene with cyanogen to form 3-(R-substituted)-2-cyano-1-propene; and
(5) brominating the 3-(R-substituted)-2-cyano-1-propene to form the desired product.

1 Claim, No Drawings

METHOD OF PREPARING 1,2-DIBROMO-2-CYANO-(SUBSTITUTED)-ALKANE ANTIMICROBIAL COMPOUNDS

BACKGROUND OF THE INVENTION

1. Field of the Invention

The present invention is concerned with a method of preparing novel compounds which are 1,2-dibromo-2-cyano-(substituted)alkanes. These novel antimicrobial compounds have a number of important industrial and agricultural applications.

As used herein, the term "antimicrobial" describes the killing of, as well as the inhibition of or control of the growth of bacteria, yeasts, fungi, and algae. A number of important industries can experience serious adverse effects from the activity of such bacteria and fungi on the raw materials which they employ, on various aspects of their manufacturing activities, or on the finished products which they produce. Such industries include the paint, wood, textile, cosmetic, leather, tobacco, fur, rope, paper, pulp, plastics, fuel, oil, rubber, and machine industries. Important applications include: inhibiting the growth of bacteria in aqueous paints, adhesives, latex emulsions, and joint cements; preserving wood; preserving cutting oils; controlling slime-producing bacteria and fungi in pulp and paper mills and cooling towers; as a spray or dip treatment for textiles and leather to prevent mold growth; as a component of anti-fouling paints to prevent adherence of fouling organisms, as a hard surface disinfectant to prevent growth of bacteria and fungi on walls, floors, etc.; and in swimming pools to prevent algae. The control of bacteria and fungi in pulp and paper mill water systems which contain aqueous dispersions of papermaking fibers is especially important. The uncontrolled buildup of slime produced by the accumulation of bacteria and fungi causes offgrade production, decreased production due to breaks and greater cleanup frequency, increased raw material usage, and increased maintenance costs. The problem of slime deposits has been aggravated by the widespread use of closed white water systems in the paper industry.

Antimicrobial compounds prepared by the method of the present invention are also utilized for agricultural applications, for example in preventing or minimizing the growth of harmful bacterial, yeast, and/or fungi on plants, trees, fruit, seeds, or soil.

2. Brief Description of the Prior Art

Lespieau et al. in *Org. Syn. I.* 209, describe preparation of 2,3-dibromopropene by dehydrobromination of 1,2,3-tribromopropane. Lespieau et al, in *Org. Syn. I,* 186 also describe coupling of a cyclohexyl group to 2,3-dibromopropene by means of cyclohexylmagnesium bromide.

Grignard, in *Compt, Rend.* 152:388–390 (1911), describes the reaction of a Grignard compound with cyanogen, but does not suggest that the Grignard compound can be unsaturated as in the method of the present invention.

Grignard et al., in *Ann. de Chim.* 4:28–57 (1915), describe in detail various reactions of Grignard compounds with cyanogen, but do not suggest that the Grignard compound can be unsaturated as in the method of the present invention.

Thus, none of the references discussed above, either singly or taken together, would suggest the novel method of preparation of the present invention.

DETAILED DESCRIPTION OF THE INVENTION AND PREFERRED EMBODIMENTS

In accordance with the present invention there is provided a method of preparing novel 1,2-dibromo-2-cyano-(substituted)alkanes of the formula:

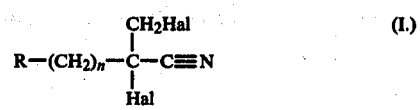

where

R is selected from the group consisting of hydrogen; $C_{1-8}$alkyl, straight or branched chain; $C_3$-$C_8$cycloalkyl; $C_{3-8}$cycloalkyl$C_{1-3}$alkyl; phenyl; phenyl$C_{1-3}$alkyl; mono- or disubstituted phenyl or phenyl$C_{1-3}$alkyl wherein the substituents are halo, $C_{1-4}$alkyl, $C_{1-4}$alkoxy, hydroxy, nitro, cyano, or trifluoromethyl; a heterocyclic radical selected from the group consisting of thienyl, furanyl, pyrrolyl, isoxazolyl, oxazolyl, isothiazolyl, thiazolyl, pyrazolyl, imidazolyl, pyridazinyl, pyrimidinyl, pyrazinyl, and pyridinyl, and N-oxides thereof; and a saturated heterocyclic radical selected from the group consisting of pyrrolidinyl, tetrahydrofuranyl, tetrahydrothienyl, isoxazolidinyl, oxazolidinyl, isothiazolidinyl, thiazolidinyl, pyrazolidinyl, imidazolidinyl, piperazinyl, and piperidinyl;

Hal is bromine or chlorine; and n is 1 to 4;

comprising the following steps:

(1) halogenating allyl halide to form 1,2,3-trihalopropane;

(2) dehydrohalogenating the 1,2,3-trihalopropane to form 2,3-dihalo-1-propene;

(3) treating the 2,3-dihalo-1-propene with a Grignard reagent of the formula R-MgHal, where R is as defined above, followed by treatment with magnesium, to form 3-(R-substituted)-2-magnesium-halide)-1-propene;

(4) treating the 3-(R-substituted)-2-(magnesium-halide)-1-propene with cyanogen to form 3-(R-substituted)-2-cyano-1-propene; and (5) brominating the 3-(R-substituted)-2-cyano-1-propene to form the desired product.

As used above, the terms "halide", "halo", "Hal", and "halogenating" refer to bromine or chlorine, and brominating or chlorinating. On a laboratory scale, bromine is the preferred halogen because of its greater reactivity. However, in a manufacturing context, chlorine would probably be the preferred halogen because of its lower cost.

The steps in the method of the present invention cover a series of reactions which may be illustrated as follows:

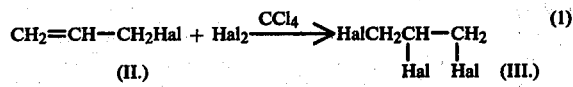

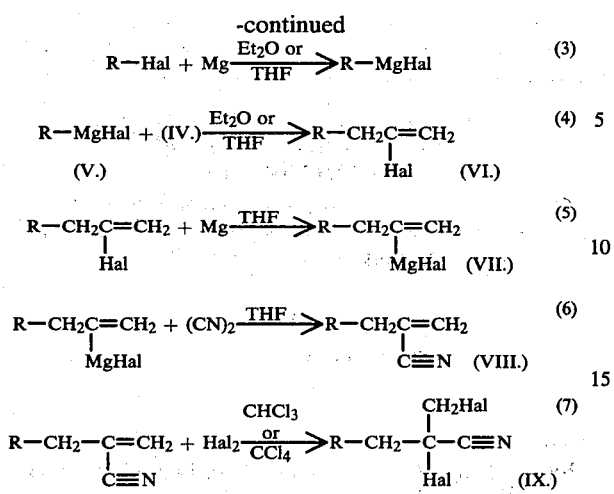

where R is as defined above.

In the first two steps shown above, the intermediate 2,3-dihalo-1-propene (IV.) is prepared from the available starting material 3-halo-1-propene (II.) by halogenation, followed by selective dehydrohalogenation.

(1) The allyl bromide or chloride starting material is treated with bromine or chlorine either neat or in a chlorinated hydrocarbon solvent such as carbon tetrachloride, chloroform, or dichloromethane. The reaction is exothermic and cooling is used to maintain the reaction temperature at about room temperature. The solvent is then removed and the liquid residue is carried forward to the next step.

(2) In the second step, dehydrobromination or dehydrochlorination is carried out using a strong base such as sodium hydroxide or potassium hydroxide. Water, the salt of the base, and the product are formed in the reaction, and the reaction is carried out with virorous boiling which results in spontaneous distillation of the product with the water, thus driving the reaction to completion.

(3) The third step involves preparation of the Grignard reagent in accordance with well known techniques.

(4) The reaction of the Grignard reagent with the propene product of the second step is exothermic, and the temperature of the reaction mixture must be kept below 15° C. in order to avoid self-coupling of the Grignard reagent and promote cross-coupling with the propene. This result can also be facilitated by the use of a catalyst such as copper (I) chloride. The solvent employed may be any inert, aprotic solvent such as diethyl ether, tetrahydrofuran, or diglyme and the like. When the reaction is complete, the solvent is removed, and the product is then separated and dissolved in a solvent for use in the next step.

(5) In the fifth step, the substituted propene from the preceding step is slowly added to magnesium turnings with vigorous stirring in order to promote solubilization of the Grignard product formed on the surface of the magnesium. The reaction is exothermic, and the reaction mixture is kept at the reflux temperature of the solvent, which is selected from the group consisting of tetrahydrofuran, diethyl ether, and diglyme. The time required for completion of the reaction depends upon the reaction temperature and upon the surface area of the magnesium, i.e., magnesium of finer mesh size will result in a faster reaction. When the reaction is complete, the reaction mixture is carried over for use in the next step without further treatment.

(6) In the sixth step cyanogenation is accomplished by reverse addition of the Grignard product of the preceding step to a saturated solution of cyanogen. It has been found that cyanogen chloride and cyanogen bromide are unacceptable reactants because they result in insignificant yields of product. Reverse addition is required in order to avoid an excess of the Grignard reactant, which can react with the product. The solvent medium in which the reaction is carried out is selected from tetrahydrofuran, diethyl ether, and diglyme. The reaction is mildly exothermic, and the reaction mixture temperature is maintained at from −20° to +20° C. in order to ensure the solubility of the cyanogen. The product is separated and carried forward to the last step.

(7) In the seventh and last step, bromination is carried out under the same conditions as described above for the first step to give the final product, which is then separated and purified.

The following example, which was actually carried out, will serve to further illustrate the method of the present invention, without at the same time, however, constituting any limitation thereof.

EXAMPLE 1

Preparation of 1,2-dibromo-2-cyano-3-phenylpropane

A. 1,2,3-Tribromopropane

The reaction was carried out in a 5000 ml 3-necked round bottomed glass flask equipped with a motor-driven paddle stirrer, water-cooled reflux condenser, thermometer and a bromine addition funnel. The flask was charged with 605 g of allyl bromide and 1250 ml of carbon tetrachloride. To this solution was added 1275 g of bromine at a rate so that the reaction temperature did not exceed 30° C. The addition was completed in about 20 hours after which time the solvent was stripped off to yield the theoretical amount of material as a heavy yellow oil. The product was used directly without further treatment in the next step.

B. 2,3-Dibromo-1-propene

A 1000 ml round bottomed flask was connected by a wide, bent glass adapter to an efficient condenser, which was provided with an adapter leading to a 500 ml receiving flask immersed in an ice bath. 600 g of 1,2,3-tribromopropane and 30 ml water were charged to the reaction flask and 150 g of sodium hydroxide as pellets was added at once. Vigorous stirring was then provided by a magnetic stirrer, and the flask was heated with a heating mantle. Heat was applied until a vigorous boiling occured resulting in a spontaneous distillation of the reaction product. The mass became solid as the volatile products were removed. Heat was continued until no more product distilled.

The distillate in the receiving flask separated into two layers: an upper layer of water and a heavy layer of a colorless oil consisting of a mixture of the desired 2,3-dibromopropene and starting material. The distillate was transferred to a 500 ml separatory funnel and the phases were separated. The organic phase was then washed with an additional 150 ml of water and dried overnight over anhydrous sodium sulfate. The crude product weighed 498 g. Fractional distillation under reduced pressure (56°–58° C./35 mm) gave 283 g (66 percent of the theoretical amount). The residue consisted mainly of unreacted 1,2,3-tribromopropane which could be recycled to the next batch.

C. 2-Bromo-3-phenyl-1-propene

A 1000 ml 3-necked round-bottomed flask was fitted with a mechanical stirrer through a mineral oil sealed bearing, a reflux condenser and 1000 ml addition funnel. A mixture of 156 g of 2,3-dibromopropene and 150 ml of dry ethyl ether was added. The flask was cooled to 0° C. in acetone/dry-ice and a solution of phenyl magnesium bromide, prepared from 18.7 g of magnesium, 120.8 g of bromobenzene, and 350 ml of dry ether was added at such a rate so that the temperature did not exceed 15° C. The addition took about one hour. Stirring was continued and the acetone/dry-ice bath was replaced with a heating mantle. The mixture was gently refluxed for 2 hours, after which time the flask was again cooled and a solution of 15 ml 36% hydrochloric acid and 150 ml water was added dropwise by means of an addition funnel. The contents of the flask were then transferred to a separatory funnel, and the ether layer was separated and dried over anhydrous sodium sulfate.

The ether was distilled off and the residue was fractionated under reduced pressure (40°–41° C./0.2–0.4 mm) yielding 48.1 g (32 percent of theory). The residue, 26 g, consisted mainly of diphenyl, m.p. 69°–71° C.

D. 2-Cyano-3-phenyl-1-propene

A 1000 ml 3-necked round-bottomed flask was fitted with a mechanical stirrer through a mineral oil sealed bearing, a reflux condenser, a thermometer, a 500 ml addition funnel, and a gas inlet tube (a static atmosphere of argon was maintained throughout the course of the reaction). 400 ml of dry tetrahydrofuran was introduced and the flask was cooled to $-10°$ C. in an acetone/dry-ice bath. The gas inlet tube was adjusted so that it extended beneath the surface of the tetrahydrofuran and 10.9 g of cyanogen was slowly bubbled in. When the addition of gas was complete, the solution was stirred and a solution of 3-phenyl-1-propene-2-magnesium bromide, prepared from 41 g of 3-phenyl-2-bromo-1-propene, 5.1 g of magnesium, and 400 ml of tetrahydrofuran, was slowly added. The addition took 1.5 hrs an the temperature was regulated so that it did not exceed 0° C. When the addition was complete stirring was continued and the reaction was allowed to come to room temperature. After stirring for 2 hours the mixture was hydrolyzed by pouring over 1 kg of crushed ice and 30 ml of 36% hydrochloric acid. After the ice melted two phases resulted, the separation of which improved after standing for several hours. The mixture was then transferred to a separatory funnel and the lower aqueous layer was separated from the organic phase. The aqueous layer was extracted with 300 ml of ethyl ether and combined with the organic layer which was then dried overnight over anhydrous sodium sulfate. After stripping off the solvents the residue was fractionally distilled under reduced pressure (68°–73° C./0.3 mm) to yield 17.1 g (57 percent of theory). A small quantity of allyl benzene, b.p. 156°–157° C. was recovered from the vacuum pump dry-ice/acetone trap.

E. 1,2-Dibromo-2-cyano-3-phenylpropane

The reaction was carried out in a 250 ml 3-necked round bottomed flask equipped with a magnetic stirrer, water-cooled reflux condenser, thermometer and a bromine addition funnel. The flask was charged with 5 g of 2-cyano-3-phenyl-1-propene and 50 ml of dry chloroform. To this solution 5.3 g of bromine was added an the mixture was stirred until the deep red color lightened. In this case the mixture was stirred for 2.5 days. After stripping off the solvent, the crude material was purified by passing through silica gel to yield 8.7 g (eighty-two percent of theory).

What is claimed is:

1. A method of preparing compounds of the formula:

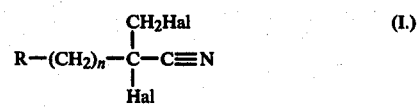

where
R is selected from the group consisting of $C_{1-8}$alkyl, straight or branched chain or phenyl;
Hal is bromine or chlorine; and
n is 1;
comprising the following steps:
(1) adding to magnesium a substituted propene of the formula:

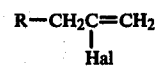

in a solvent medium, selected from the group consisting of tetrahydrofuran, diethylether and diglyme, to form 3-(R-substituted)-2-(magnesium halide)-1-propene;
(2) reacting the 3-(R-substituted)-2-(magnesium halide)-1-propene with cyanogen in a reverse addition reaction in a solvent medium, selected from the group consisting of tetrahydrofuran, diethylether and diglyme, to form 3-(R-substituted)-2-cyano-1-propene; and
(3) halogenating with substantially equimolar amount of halogen the 3-(R-substituted)-2-cyano-1-propene to form the desired product.

* * * * *